(12) United States Patent
Fagan

(10) Patent No.: US 11,369,422 B1
(45) Date of Patent: Jun. 28, 2022

(54) BONE FIXATION TANGS WITH SELF-BALANCING EXTENSION

(71) Applicant: Orthopedic Designs North America, Inc., Tampa, FL (US)

(72) Inventor: Lance Fagan, Tampa, FL (US)

( * ) Notice: Subject to any disclaimer, the term of this patent is extended or adjusted under 35 U.S.C. 154(b) by 0 days.

(21) Appl. No.: 17/121,842

(22) Filed: Dec. 15, 2020

(51) Int. Cl.
*A61B 17/72* (2006.01)

(52) U.S. Cl.
CPC .................. *A61B 17/7266* (2013.01)

(58) Field of Classification Search
CPC ............ A61B 17/72–7291; A61B 17/844
See application file for complete search history.

(56) References Cited

U.S. PATENT DOCUMENTS

| | | | | |
|---|---|---|---|---|
| 3,986,504 A * | 10/1976 | Avila | .................. | A61B 17/7225 606/63 |
| 5,534,004 A * | 7/1996 | Santangelo | .......... | A61B 17/742 606/68 |
| 5,702,215 A * | 12/1997 | Li | ....................... | F16B 13/0866 411/21 |
| 5,839,769 A * | 11/1998 | Slocum | .................. | B65G 47/26 294/87.1 |
| 6,245,075 B1 * | 6/2001 | Betz | .................... | A61B 17/7216 606/105 |
| 6,575,973 B1 * | 6/2003 | Shekalim | ........... | A61B 17/7225 606/62 |
| 8,133,226 B2 * | 3/2012 | Chou | .................. | A61B 17/7266 606/63 |
| 8,491,584 B1 * | 7/2013 | Fagan | ................. | A61B 17/7266 606/64 |
| 9,827,025 B2 * | 11/2017 | Jansen | ................ | A61B 17/7258 |
| 2006/0229617 A1 * | 10/2006 | Meller | ............... | A61B 17/7266 606/62 |
| 2010/0204735 A1 * | 8/2010 | Gephart | ............. | A61B 17/7037 606/264 |
| 2015/0038968 A1 * | 2/2015 | Vega | ................... | A61B 17/7266 606/64 |

\* cited by examiner

*Primary Examiner* — Eduardo C Robert
*Assistant Examiner* — Steven J Cotroneo
(74) *Attorney, Agent, or Firm* — Larson & Larson, P.A.; Justin P. Miller; Frank Liebenow

(57) ABSTRACT

The bone fixation tangs with self-balancing extension compensate for the internal cavity shape of the intramedullary canal, thus avoiding the related issues of over-extension and under-extension of tangs. Over-extension, or pushing the tangs too deeply in the inner wall of the bone, is unnecessarily traumatic to the patient and may weaken the bone. Under-extension, or stopping extension before the tangs have locked into the interior surface of the bone, results in reduced mechanical strength, thus compromising the ability of the nail to provide support to the bone. The bone fixation tangs with self-balancing extension address this issue by allowing the tangs to balance their extension.

14 Claims, 4 Drawing Sheets

Symmetric Talon Deployment within a Proximal Flare Provides Uneven Load Distribution Asymmetric Talon Deployment within a Proximal Flare Provides Even Load Distribution

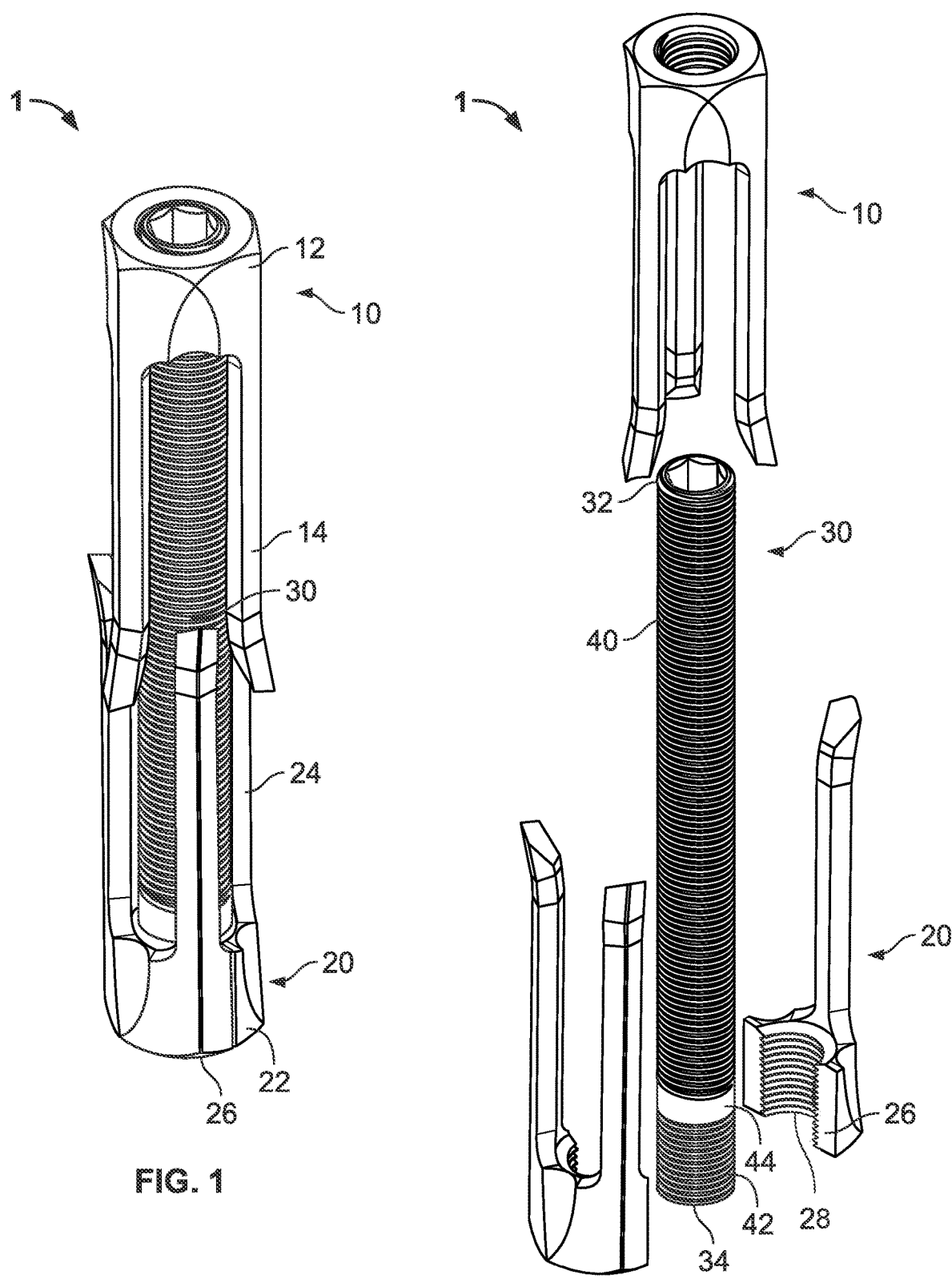

Symmetric Talon Deployment within a Distal Flare Provides Uneven Load Distribution Asymmetric Talon Deployment within a Distal Flare Provides Even Load Distribution

BONE FIXATION TANGS WITH SELF-BALANCING EXTENSION

FIELD

This invention relates to the field of bone implants for placement within intramedullary canals, specifically a mechanism for fixation.

BACKGROUND

Bone implants, or nails, act to augment the structure of a bone, correcting a fracture or other defect. While nails are considered superior to plates, rotation of the nails within the bone, specifically the intramedullary canal—the inside of a bone—can be a problem.

This problem was initially solved by the installation of screws through the bone, passing through the nail within the bone. But the installation of screws caused further trauma to the patient, while increasing the complexity of the surgery.

The solution was internal tangs that extend into the bone after placement of the nail.

While this methodology avoids the addition of screws, the prior art tang extension mechanisms cannot adapt to the internal structure of the bone.

What is needed is a mechanism for extension of tangs within the bone, the mechanism adapting to the internal structure of the bone.

SUMMARY

The bone fixation tangs with self-balancing extension compensate for the internal cavity shape of the intramedullary canal, thus avoiding the issues of over-extension and under-extension of tangs.

Over-extension, or pushing the tangs too deeply in the inner wall of the bone, is unnecessarily traumatic to the patient and may weaken the bone.

Under-extension, or stopping extension before the tangs have locked into the interior surface of the bone, results in reduced mechanical strength, thus compromising the ability of the nail to provide support to the bone.

The bone fixation tangs with self-balancing extension address this issue by allowing the tangs to balance their extension.

In the prior art, both sets of tangs are forced outward symmetrically, or in parallel—their extensions matching in magnitude.

This symmetric extension is generally achieved by the tangs having threaded hubs, the hubs translating the rotational movement of a central screw into linear movement.

The central screw is fixed, and the threading of the hubs matches each other and the central screw.

Thus, the central screw rotation causes equal and matching linear movement of the hubs, resulting in equal and matching linear movement of the tangs, and thus equal extension. This methodology is acceptable for a cylindrical intramedullary canal of consistent shape. But in practice, such a perfect interior surface is rare, and thus symmetric extension is an imperfect solution.

In contrast to symmetric extension, the tangs of the bone fixation tangs with self-balancing extension need not extend symmetrically, but can extend asymmetrically. This is achieved by allowing linear motion of the central screw, or tang actuation shaft, and using zero-lead threads on one tang hub, thus fixing the tang hub to the tang actuation shaft linearly/translationally, but still permitting free rotation.

In the disclosed embodiment, the first tang set uses a threaded hub with threads having a non-zero lead, lead being the amount of axial or linear advance of during one complete rotation. Stated differently, rotation of the hub causes linear motion of the hub with respect to the tang actuation shaft.

The second tang set uses a threaded hub with threads having a zero lead. Stated differently, rotation of the hub along its associated threads does not cause linear motion—the rotation of the screw does not cause the hub to move with along the tang actuation shaft.

Thus, the tang actuation shaft can rotate with respect to the second tang hub, and the actuation shaft and tang hub maintain the same linear position.

Correspondingly, if the actuation shaft moves up or down, it will carry the second tang set with it.

This combination of a first tang set that moves with respect to the actuation shaft, and the second tang set that does not, results in a balancing effect.

If during extension, the first tang set contacts the interior surface of the bone, the first tang set stops extending. Continued rotation of the actuation shaft carries the second tang set toward the first tang set, continuing its extension until the second set of tangs is placed.

Conversely, if during extension the second set of tangs contacts the interior surface of the bone, the second tang set stops extending.

Continued rotation of the actuation shaft causes no upward/downward movement of the actuation shaft, but carries the first tang set toward the second tang set, continuing its extension until the first set of tangs is placed.

In this manner, tang extension is balanced even in tapering or expanding bone cavities.

BRIEF DESCRIPTION OF THE DRAWINGS

The invention can be best understood by those having ordinary skill in the art by reference to the following detailed description when considered in conjunction with the accompanying drawings in which:

FIG. 1 illustrates an assembled, but unactuated view, of the bone fixation tangs with self-balancing extension.

FIG. 2 illustrates a disassembled view of the bone fixation tangs with self-balancing extension.

DETAILED DESCRIPTION

Figure 3:
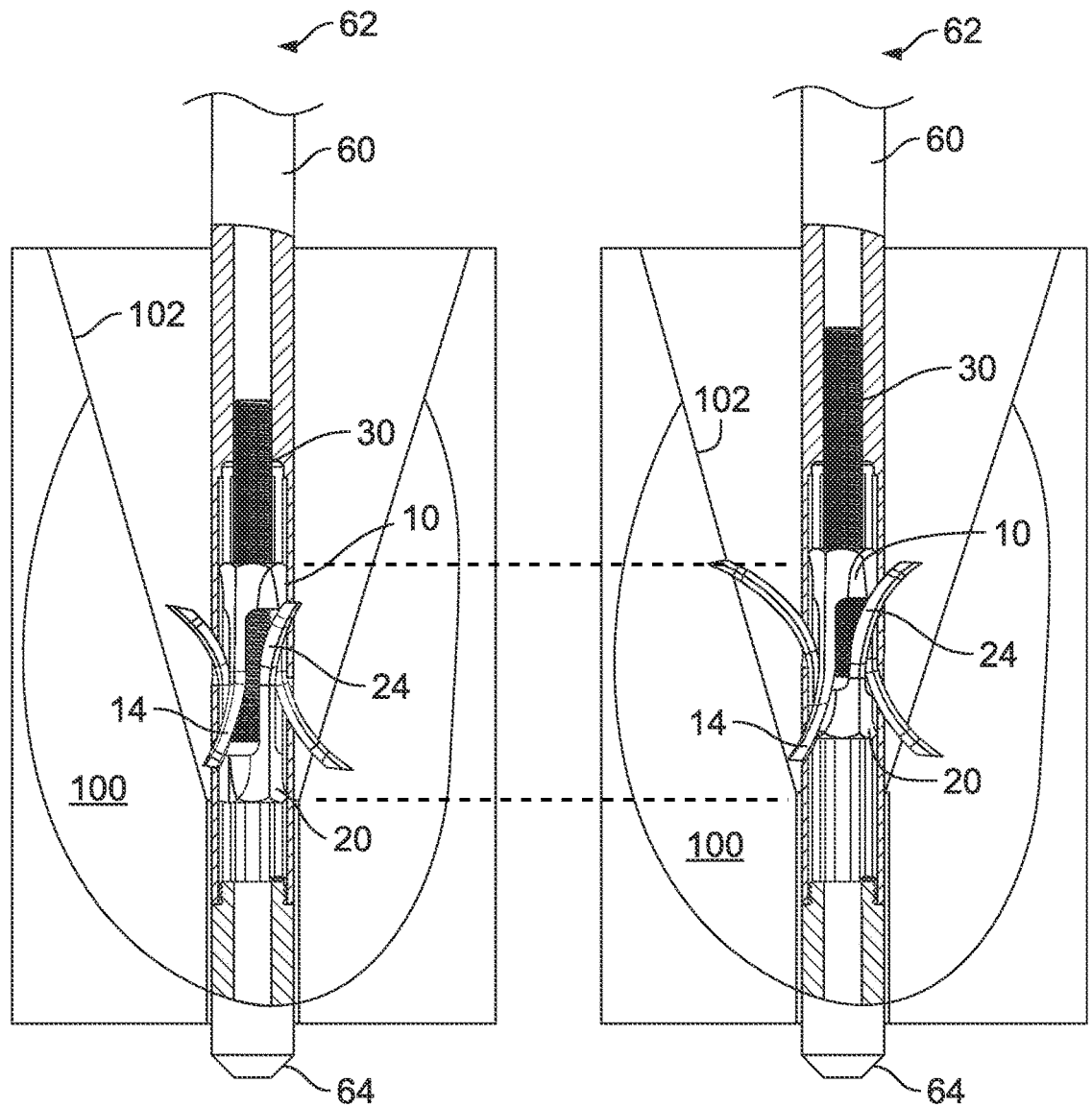
FIG. 3 illustrates a third view showing both symmetric and asymmetric actuation of the bone fixation tangs with self-balancing extension.

Reference will now be made in detail to the presently preferred embodiments of the invention, examples of which are illustrated in the accompanying drawings. Throughout the following detailed description, the same reference numerals refer to the same elements in all figures.

Referring to FIGS. 1 and 2, an assembled, but unactuated view, and disassembled view of the bone fixation tangs with self-balancing extension are shown.

The bone fixation tangs with self-balancing extension 1 are shown with first nail tang set 10 formed from first nail tang hub 12, and first nail tang prongs 14.

The second nail tang set 20 is formed from second nail tang hub 22 and second nail tang prongs 24. The second nail tang hub 22 includes second nail tang set threads 28 with no lead, which thus cannot be threaded onto the tang actuation shaft 30. Instead, the second nail tang hub 22 is split at the second nail tang hub mating surface 26 to allow placement of the second nail tang hub 22 over the tang actuation shaft 30.

The second tang hub 22 is preferably held against the tang actuation shaft 30 by the nail body 60, or intramedullary nail (see FIG. 3). Stated differently, the interior channel of the nail body 60 prevents the second tang hub 22 from separating at the mating surface 26, thus keeping the second tang hub 22 in contact with the second set of threads 42 of the tang actuation shaft 30.

Referring to FIG. 3, a third view showing both symmetric and asymmetric actuation of the bone fixation tangs with self-balancing extension is shown.

The nail body 60 is shown with nail proximal end 62 and nail distal end 64. The first nail tang set 10 includes first nail tang prongs 14, and the second nail tang set 20 includes second nail tang prongs 24.

The tang prongs 14/24 exit the nail body 60 through tang portals 70.

The figures are a combination of 3D and 2D representations. The nail body 60 is shown in 2D cross-section, as is the bone 100. But the tangs 14/24 are shown in 3D. Thus, even when over-embedment is shown, this may not be immediately apparent for all tangs because some tangs 14/24 are projecting upward, out of the figure.

On the left of FIG. 3, standard tangs are shown, where the extension is symmetric regardless of bone shape. Here, with a proximal flare, the second nail tang prongs 24 have further to travel as compared to the first nail tang prongs 14. But with symmetric extension, the first nail tang prongs 14 over-extend, but the second nail tang prongs 24 under-extend.

On the right of FIG. 3, the asymmetric extension, or self-balancing extension, shown on the right balances the tangs. Here the second nail tang prongs 24 can extend more than the first nail tang prongs 14, causing even embedment into the bone 100, the nail body 60 within the intramedullary canal 102. By referencing the dashed horizontal lines, one can see that the first nail tang set 10 has descended further into the nail body 60, forcing greater extension of the first nail tang prongs 14. The tang actuation shaft 30 is in a nearly identical position because the second nail tang set 20 is in a similar final position.

Figure 4:
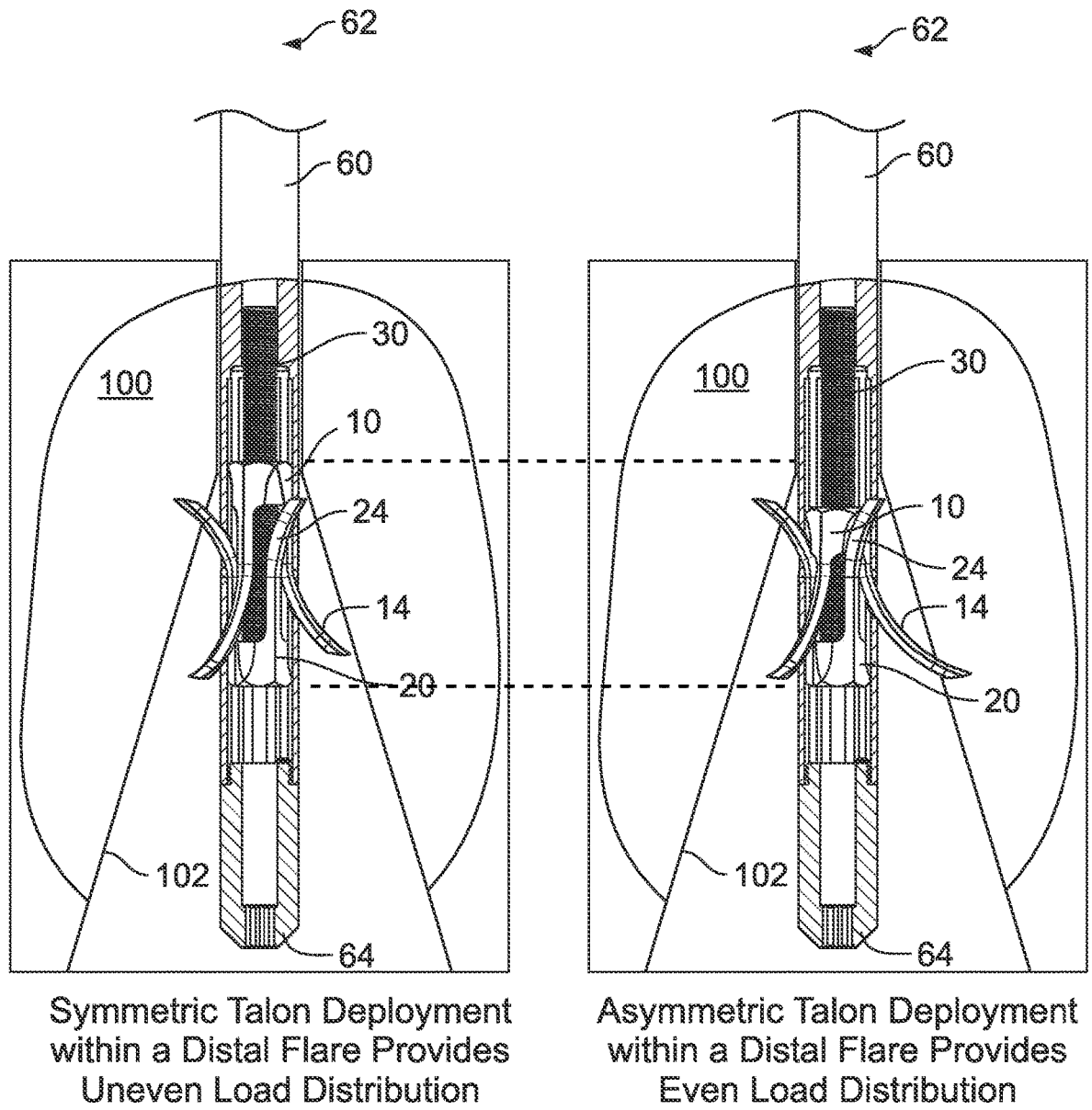
FIG. 4 illustrates a fourth view showing both symmetric and asymmetric actuation of the bone fixation tangs with self-balancing extension.

Referring to FIG. 4, a fourth view showing both symmetric and asymmetric actuation of the bone fixation tangs with self-balancing extension is shown.

Similarity to FIG. 3, but with a distal flare rather than a proximal flare, the self-balancing tangs 14/24 again improve performance.

On the left of FIG. 4, standard tangs are shown, where the extension is symmetric regardless of bone shape. Here, with a distal flare, the second nail tang prongs 24 need to travel less as compared to the first nail tang prongs 14. But with symmetric extension, the first nail tang prongs 14 under-extend, while the second nail tang prongs 24 over-extend.

On the right of FIG. 4, the asymmetric extension, or self-balancing extension, shown on the right balances the tangs. Now the first nail tang prongs 14 can extend more than the second nail tang prongs 24, causing even embedment into the bone 100. By referencing the dashed horizontal lines, one can see that the second nail tang set 20 has risen with respect to the nail body 60, forcing greater extension of the second nail tang prongs 24. The tang actuation shaft 30 has correspondingly risen because it is fixed linearly with the second nail tang hub 22.

Figure 5:
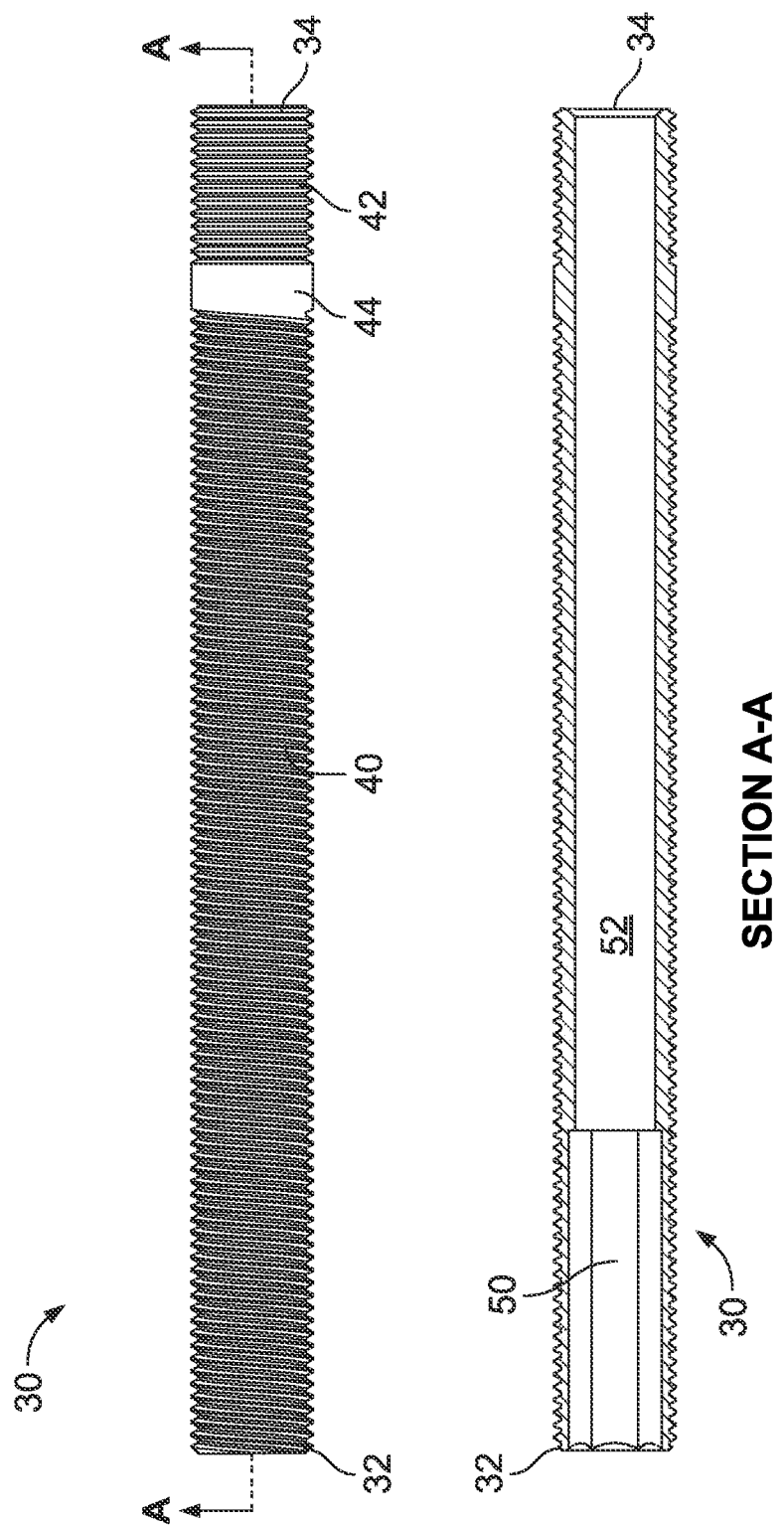
FIG. 5 illustrates an outer and cross-sectional view of the tang actuation shaft of the bone fixation tangs with self-balancing extension.

Referring to FIG. 5, an outer and cross-sectional view of the tang actuation shaft of the bone fixation tangs with self-balancing extension is shown.

The tang actuation shaft 30 includes proximal shaft end 32 and distal shaft end 34.

The outer surface of tang actuation shaft 30 includes a first set of threads 40 and a second set of threads 42, separated by a non-threaded separation 44.

The first set of threads 40 is shown with a non-zero lead—each rotation causes linear movement. The second set of threads 42 is shown without a lead, or with a zero-lead, thus the second set of threads 42 is circumferential. Each individual thread of the second set of threads 42 is disconnected from its neighbors, rather forming a circle with itself around the tang actuation shaft 30.

A socket head 50 is shown for actuation, with a full cannulation 52 to allow for passing the bone fixation tangs with self-balancing extension 1 over a guide wire.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A device for balancing extension of tangs inside an intramedullary canal of a bone, the device comprising:
   a tang actuation shaft within an intramedullary nail;
      the tang actuation shaft is able to slide linearly, without rotation, within the intramedullary nail;
   a first nail tang set with first nail tang prongs;
      the first nail tang set interfacing with the tang actuation shaft such that rotation of the tang actuation shaft causes the first nail tang set to move linearly with respect to the tang actuation shaft;
   a second nail tang set with second nail tang prongs;
      the second nail tang set interfacing with the tang actuation shaft such that rotation of the tang actuation shaft does not cause the second nail tang set to move linearly with respect to the tang actuation shaft;
   whereby the extension of the first nail tang prongs and second nail tang prongs adapts to a shape of the intramedullary canal, thus avoiding under-extension or over-extension.

2. The device of claim 1, wherein:
   the first nail tang set interfaces with the tang actuation shaft at a first set of threads;
      the first set of threads having a non-zero lead, thus rotation causes linear movement;
   the second nail tang set interfaces with the tang actuation shaft at a second set of threads;
      the second set of threads having a zero lead, thus rotation does not cause linear movement;

the tang actuation shaft is permitted to move up and down within the intramedullary nail while it balances extension between the first nail tang set and the second nail tang set.

3. The device of claim 1, further comprising:
a second nail tang set hub;
   the second nail set hub integrated with the second nail tang set;
   the second nail tang set hub separable into two or more pieces;
whereby the second nail tang hub is installed by being placed around the tang actuation shaft.

4. The device of claim 3, wherein:
the two or more pieces of the second nail tang set hub are held against the tang actuation shaft by being contained within the intramedullary nail.

5. The device of claim 1, wherein:
the device is fully cannulated;
whereby a guide wire can be passed fully through the device, thus aiding in placement.

6. A device for fixation of a nail body inside an intramedullary canal, the device including:
a first nail tang set with first nail tang prongs and a second nail tang set with second nail tang prongs;
the first nail tang set and the second nail tang set interfacing with a tang actuation shaft;
rotation of the tang actuation shaft does cause linear movement of the first nail tang set with respect to the tang actuation shaft;
rotation of the tang actuation shaft does not cause linear movement of the second nail tang set with respect to the tang actuation shaft;
   the tang actuation shaft is able to slide linearly, without rotation, within the nail body;
whereby because the first nail tang set and the second nail tang set behave differently upon the application of rotation by the tang actuation shaft, and the tang actuation shaft is able to slide within the nail body, the first nail tang prongs and the second nail tang prongs balance extension inside the intramedullary canal.

7. The device of claim 6, wherein:
the first nail tang set interfaces with the tang actuation shaft at a first set of threads;
   the first set of threads having a non-zero lead, thus rotation causes linear movement;
the second nail tang set interfaces with the tang actuation shaft at a second set of threads;
   the second set of threads having a zero lead, thus rotation does not cause linear movement;
the tang actuation shaft is permitted to move up and down within the intramedullary nail while it balances extension between the first nail tang set and the second nail tang set.

8. The device of claim 6, further comprising:
a second nail tang set hub;
   the second nail set hub integrated with the second nail tang set;
   the second nail tang set hub separable into two or more pieces;
whereby the second nail tang hub is installed by being placed around the tang actuation shaft.

9. The device of claim 8, wherein:
the two or more pieces of the second nail tang set hub are held against the tang actuation shaft by being contained within the nail.

10. The device of claim 6, wherein:
the device is fully cannulated;
whereby a guide wire can be passed fully through the device, thus aiding in placement.

11. A device for balancing the extension of tangs inside an irregularly shaped bone cavity, the device comprising:
a nail body;
a tang actuation shaft slidably interfacing with the nail body;
a first nail tang set with a first set of nail tang threads;
   the first nail tang set interfacing with the tang actuation shaft via the first set of nail tang threads;
   the first set of nail tang threads having non-zero lead, thus rotation does not cause linear movement;
a second nail tang set with a second set of nail tang threads;
   the second nail tang set interfacing with the tang actuation shaft via the second set of nail tang threads;
   the second set of nail tang threads having zero lead, thus rotation does not cause linear movement;
whereby differing action of the first nail tang set and the second nail tang set creates a self-balancing action, allowing the tangs to extend while the tang actuation shaft maintains a fixed linear position with respect to the nail body, resulting in ideal extension of the tangs.

12. The device of claim 11, further comprising:
a second nail tang set hub;
   the second nail set hub integrated with the second nail tang set;
   the second nail tang set hub separable into two or more pieces;
whereby the second nail tang hub is installed by being placed around the tang actuation shaft.

13. The device of claim 12, wherein:
the two or more pieces of the second nail tang set hub are held against the tang actuation shaft by being contained within an intramedullary nail.

14. The device of claim 11, wherein:
the device is fully cannulated;
whereby a guide wire can be passed fully through the device, thus aiding in placement.

\* \* \* \* \*